United States Patent
Ishiguro et al.

(10) Patent No.: US 9,518,954 B2
(45) Date of Patent: Dec. 13, 2016

(54) GAS SENSOR CONTROL DEVICE

(75) Inventors: Yasuhiro Ishiguro, Aichi (JP); Satoru Abe, Aichi (JP); Akihiro Kobayashi, Aichi (JP); Takayuki Sumi, Aichi (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 1205 days.

(21) Appl. No.: 12/265,363

(22) Filed: Nov. 5, 2008

(65) Prior Publication Data
US 2009/0120161 A1 May 14, 2009

(30) Foreign Application Priority Data

Nov. 5, 2007 (JP) ................................ P2007-287238

(51) Int. Cl.
*G01N 27/417* (2006.01)

(52) U.S. Cl.
CPC ................................. *G01N 27/4175* (2013.01)

(58) Field of Classification Search
CPC ................................................. G01N 27/4175
USPC ............. 204/406, 424; 205/781, 784.5, 785; 73/23.31
See application file for complete search history.

(56) References Cited

U.S. PATENT DOCUMENTS

| 5,311,447 | A | 5/1994 | Bonne |
| 6,228,252 | B1 | 5/2001 | Miyata et al. |
| 6,533,921 | B2 | 3/2003 | Miyata et al. |
| 6,635,161 | B2 * | 10/2003 | Inagaki .................... 204/425 |
| 2003/0106808 | A1 | 6/2003 | Miyata et al. |
| 2003/0121310 | A1 * | 7/2003 | Tomura ................ G01N 27/419 73/31.05 |
| 2005/0197795 | A1 * | 9/2005 | Aas et al. ...................... 702/107 |

FOREIGN PATENT DOCUMENTS

| EP | 0937979 A2 | 8/1999 |
| JP | 10-288595 A | 10/1998 |
| JP | 11-304758 A | 11/1999 |
| JP | 2001-91296 A | 4/2001 |
| WO | 02/29909 A1 | 4/2002 |

OTHER PUBLICATIONS

Extended European Search Report dated Mar. 12, 2009.

* cited by examiner

*Primary Examiner* — Susan D Leong
(74) *Attorney, Agent, or Firm* — Sughrue Mion, PLLC

(57) ABSTRACT

A gas sensor control device for controlling a gas sensor, the gas sensor including a gas sensor element that includes a cell including a pair of electrodes and a solid electrolyte, the gas sensor control device including a circuit board connectable to the gas sensor. The circuit board has mounted thereon a voltage control unit mounted on the circuit board and configured to control a voltage developed across a pair of electrodes of the cell to a constant voltage; a temperature detecting unit mounted on the circuit board and configured to detect a temperature of the circuit board; and a voltage correcting unit mounted on the circuit board and configured to apply a correction voltage to the voltage control unit compensating for a temperature-dependent variation in the constant voltage based on the temperature detected by the temperature detecting unit.

6 Claims, 10 Drawing Sheets

FIG. 6

LOW-TEMPERATURE SIDE (35°C OR LESS)

| CORRECTION RANK | Vs CONTROL VOLTAGE CORRECTION AMOUNT DUTY [%] | | | |
|---|---|---|---|---|
| | −40〜−25°C | −25〜−5°C | −5〜15°C | 15〜35°C |
| 0 | 2.7 | 1.6 | 0.8 | 0 |
| 1 | 2.4 | 1.6 | 0.8 | 0 |
| 2 | 2.0 | 1.2 | 0.4 | 0 |
| 3 | 1.6 | 0.8 | 0.4 | 0 |
| 4 | 1.2 | 0.8 | 0.4 | 0 |
| 5 | 0.8 | 0.4 | 0.0 | 0 |
| 6 | 0.4 | 0.0 | 0.0 | 0 |
| 7 | 0.0 | 0.0 | 0.0 | 0 |
| 8 | 0.0 | 0.0 | 0.0 | 0 |
| 9 | −0.4 | 0.0 | 0.0 | 0 |
| 10 | −0.8 | −0.4 | 0.0 | 0 |
| 11 | −1.2 | −0.8 | −0.4 | 0 |
| 12 | −1.6 | −0.8 | −0.4 | 0 |
| 13 | −2.0 | −1.2 | −0.4 | 0 |
| 14 | −2.4 | −1.6 | −0.8 | 0 |
| 15 | −2.7 | −1.6 | −0.8 | 0 |

FIG. 7

HIGH-TEMPERATURE SIDE (MORE THAN 35°C)

| CORRECTION RANK | Vs CONTROL VOLTAGE CORRECTION AMOUNT DUTY [%] | | | |
|---|---|---|---|---|
| | 35~55°C | 55~75°C | 75~95°C | 95~105°C |
| 0 | 0.0 | 0.8 | 1.6 | 2.7 |
| 1 | 0.0 | 0.8 | 1.6 | 2.4 |
| 2 | 0.0 | 0.4 | 1.2 | 2.0 |
| 3 | 0.0 | 0.4 | 0.8 | 1.6 |
| 4 | 0.0 | 0.4 | 0.8 | 1.2 |
| 5 | 0.0 | 0.0 | 0.4 | 0.8 |
| 6 | 0.0 | 0.0 | 0.0 | 0.4 |
| 7 | 0.0 | 0.0 | 0.0 | 0.0 |
| 8 | 0.0 | 0.0 | 0.0 | 0.0 |
| 9 | 0.0 | 0.0 | 0.0 | -0.4 |
| 10 | 0.0 | 0.0 | -0.4 | -0.8 |
| 11 | 0.0 | -0.4 | -0.8 | -1.2 |
| 12 | 0.0 | -0.4 | -0.8 | -1.6 |
| 13 | 0.0 | -0.4 | -1.2 | -2.0 |
| 14 | 0.0 | -0.8 | -1.6 | -2.4 |
| 15 | 0.0 | -0.8 | -1.6 | -2.7 |

GAS SENSOR CONTROL DEVICE

BACKGROUND OF THE INVENTION

1. Field of the Invention

The present invention relates to a gas sensor control device used for controlling a gas sensor. The gas sensor includes a gas sensor element configured to detect the concentration of a specific gas component in an exhaust or combustion gas of a combustor, an internal-combustion engine, etc.

2. Description of the Related Art

An air-fuel ratio sensor or an oxygen sensor for detecting concentration of oxygen in exhaust gas is known as a gas sensor for controlling combustion or improving fuel efficiency of an internal-combustion engine of a vehicle. In addition, in response to the need for reducing the amount of nitrogen oxide ($NO_x$) in exhaust gas so as to meet strict exhaust gas regulations of a vehicle, an $NO_x$ sensor capable of directly measuring concentration of $NO_x$ has been developed.

This kind of gas sensor includes a gas sensor element including one or more cells each including an oxygen ion conductive solid electrolyte such as zirconia and a pair of electrodes formed on the solid electrolyte. The concentration of the specific gas is detected based on an output of the gas sensor element.

For example, in an $NO_x$ sensor, oxygen in a first measurement chamber communicating with a measurement gas space is pumped out by a first pump cell; an oxygen concentration detecting cell measures oxygen concentration in the first measurement chamber; and the first pumping cell is controlled such that the oxygen concentration in the first measurement chamber maintains a predetermined oxygen concentration. Further, the gas to be measured having a controlled oxygen concentration flows from the first measurement chamber into a second measurement chamber, and a constant voltage is applied to a second pumping cell so as to separate $NO_x$ in the gas to be measured into $N_2$ and $O_2$. At this time, a second pump current flowing through a pair of electrodes of the second pumping cell is measured to detect the concentration of $NO_x$ in the gas to be measured.

In such an $NO_x$ sensor, it is necessary to provide a voltage control circuit for controlling the voltage developed across the electrodes of the oxygen concentration detecting cell or the second pumping cell to maintain the same at a constant voltage. For this reason, a control circuit unit (gas sensor control device) has been developed (JP-A-11-304758).

Further, since the output voltage developed across the cells changes with a change in sensor temperature, the gas detection result changes as well. To deal with this circumstance, JP-A-10-288595 (paragraphs [0073] to [0075]) describes a gas sensor control device that adds a sensor temperature correction amount to the second pump current indicating the $NO_x$ concentration, and then outputs a corrected $NO_x$ signal.

Incidentally, the gas sensor control device for controlling a gas sensor such as the $NO_x$ sensor includes a circuit board connected to the gas sensor via a signal line. On the circuit board, many electronic components (an OP Amp (operational amplifier), a resistor, etc.) constituting the voltage control circuit are mounted. In the gas sensor control device, the voltage control circuit (electronic component and the like) mounted on the circuit board is adjusted so that the voltage developed across the electrodes of the cell is maintained at a constant value before shipping the gas sensor control device. However, such adjustment is carried out only at regular temperatures. For this reason, when a temperature variation occurs at the circuit board in practical use, the control voltage may change (drift). This can happen when a characteristic of the electronic component changes with a change in temperature. In this case, it may not be possible to obtain satisfactory precision in gas concentration detection.

Although JP-A-10-288595 describes a countermeasure against gas detection result variations depending on sensor temperature, the temperature variation of the circuit board is not considered. For this reason, there is a need to solve the problem of control voltage variation due to temperature variation in order to improve the precision of gas concentration detection.

SUMMARY OF THE INVENTION

The present invention was made in consideration of the above circumstances, and an object thereof is to provide a gas sensor control device capable of improving the detection precision of the concentration of a specific gas component even when a characteristic of a voltage control unit mounted on a circuit board for maintaining a cell at a constant voltage changes with a change in temperature of the circuit board.

In a first aspect, the present invention provides a gas sensor control device for controlling a gas sensor, said gas sensor comprising a gas sensor element including a cell comprising a solid electrolyte and a pair of electrodes disposed on the solid electrolyte for detecting a concentration of a specific gas component, said gas sensor control device comprising: a circuit board connectable to the gas sensor via a signal line; a voltage control unit mounted on the circuit board and configured to control a voltage developed across the pair of electrodes of the cell to a constant voltage; a temperature detecting unit mounted on the circuit board and configured to detect a temperature of the circuit board; and a voltage correcting unit mounted on the circuit board and configured to apply a correction voltage to the voltage control unit compensating for a temperature-dependent variation in the level of the constant voltage based on the temperature detected by the temperature detecting unit.

According to the first aspect of the invention, even when a characteristic of an electronic component (circuit) of the voltage control unit mounted on the circuit board changes due to a variation in temperature, since the voltage correcting unit corrects a variation (drift) in the constant voltage, it is possible to improve precision in detection of the concentration of the specific gas based on the output signal from the gas sensor element.

A plurality of control target cells may be provided in accordance with the configuration of the gas sensor element. In the gas sensor control device used for controlling the gas sensor including such a gas sensor element, a configuration is known in which the voltage control units may be respectively connected to two control target cells selected from the plurality of control target cells. Then, in such a gas sensor control device, the correction voltage for compensating a temperature-dependent variation in the constant voltage may be applied to each of the voltage control units based on the temperature detected by the temperature detecting unit. In this manner, it is possible to improve precision in detection of the concentration of the specific gas component even when the characteristic of the electronic component mounted on the circuit board changes with a change in temperature. However, since it is necessary to provide a plurality of voltage correcting units corresponding to the number of voltage control units, the cost of the gas sensor control device increases.

Therefore, in the gas sensor control device provided with a plurality of voltage control units, the configuration according to a second aspect of the invention may be employed as a correction voltage applying unit. Specifically, in this second aspect, the invention provides a gas sensor control device according to the first aspect, wherein: the gas sensor element comprises a plurality of the control target cells; a plurality of the voltage control units are provided on the circuit board and connected to two control target cells selected from the plurality of control target cells, the voltage control units being configured to maintain the voltage developed across each of the pairs of electrodes of the selected control target cells constant; and the voltage correcting unit applies a correction voltage to the voltage control unit connected to one of the selected control target cells based on the temperature detected by the temperature detecting unit, the correction voltage compensating a temperature-dependent variation in a voltage difference between the voltage developed across the pair of electrodes of one of the two selected control target cells and the voltage developed across the pair of electrodes of the other of the two selected control target cells.

According to the above second aspect of the invention, since a variation (drift) in the voltage difference between the two control target cells is corrected even when a characteristic of the electronic component (circuit) mounted on the circuit board changes with a change in temperature, it is possible to improve precision in detection of the concentration of the specific gas component based on the output signal from the gas sensor. This is accomplished without providing a number of voltage correcting units equal to the number of the control target cells. Additionally, the control target voltages of the two or more control target cells are not limited to the same value, but may be set to constant voltages having different values for each control target cell (for example, a case where the control target voltage of one control target cell is 450 mV, and a control target voltage of the other control target cell is 425 mV).

In a third aspect, the present invention provides a gas sensor control device according to the second aspect of the invention, wherein the gas sensor element is an $NO_x$ sensor element comprising: a first solid electrolyte exposed to an atmosphere outside of the gas sensor element; one or more second solid electrolyte layers laminated in the gas sensor element and spaced apart from the first solid electrolyte; a first measurement chamber defined between the first solid electrolyte and the second solid electrolyte; a second measurement chamber communicating with the first measurement chamber; an oxygen concentration detecting cell comprising: a detection electrode contacting the first solid electrolyte or the second solid electrolyte and exposed to the first measurement chamber; and a reference electrode paired with the detection electrode and exposed to a reference atmosphere, the oxygen concentration detecting cell being configured to generate an electromotive force in response to oxygen concentration of the first measurement chamber; a first pumping cell comprising: a first inner pump electrode contacting the first solid electrolyte and exposed to the first measurement chamber; and an electrode paired with the first inner pump electrode, the first pumping cell being configured to pump oxygen into or out of the gas to be measured that is introduced into the first measurement chamber such that the electromotive force generated by the oxygen concentration detecting cell is maintained at a first constant voltage; and a second pumping cell comprising: a second inner pump electrode contacting the second solid electrolyte and exposed to the second measurement chamber; and a second outer pump electrode paired with the second inner pump electrode and disposed outside the second measurement chamber, wherein a current flows through the second pumping cell in response to $NO_x$ concentration in the second measurement chamber when a second constant voltage is applied across the second inner pump electrode and the second outer pump electrode. The second solid electrolyte of the oxygen concentration detecting cell and the second pumping cell is the same layer or may form two different layers. The control target cells are the oxygen concentration detecting cell and the second pumping cell. The voltage correcting unit applies the correction voltage to the voltage control unit connected to the oxygen concentration detecting cell, the correction voltage compensating a temperature variation of the voltage difference between inter-electrode voltages of the control target cells. Accordingly, the variation (drift) of the voltage difference between the inter-electrode voltages of the two control target cells (the oxygen concentration detecting cell and the second pumping cell) is corrected even when the characteristic of the electronic component (circuit) mounted on the circuit board changes due to a change in temperature. Thus, it is possible to improve precision in detecting the $NO_x$ concentration based on the output signal (current in accordance with the $NO_x$ concentration) from the gas sensor element just by connecting the voltage correcting unit to the oxygen concentration detecting cell.

In a forth aspect, the present invention provides a gas sensor control device according to any of the first to third aspects, wherein the gas sensor comprises a heater configured to heat the gas sensor element; wherein the gas sensor control device further comprises a heater control unit, typically mounted on the circuit board, and configured to control current supplied to the heater; and wherein the temperature detecting unit is disposed on the circuit board closer to the voltage control unit than the heater control unit.

According to the third aspect, the temperature detecting unit can detect a temperature in the vicinity of the voltage control unit on the circuit board with high precision. In addition, the detected temperature can be used for compensating a temperature-dependent variation in the constant voltage or in the voltage difference between the voltage developed across the electrodes of the first cell and the voltage developed across the electrodes of the second cell. Therefore, the compensation precision is improved.

In a fifth aspect, the present invention provides a gas sensor control device according to any of the first to fourth aspects further including a storage unit in which correction values corresponding to the correction voltage are stored in association with the temperature, wherein the voltage correcting unit applies the correction voltage to the voltage control unit based on the correction value associated with the temperature detected by the temperature detecting unit.

In accordance with a sixth aspect, a storage unit may store correction values for each of predetermined temperature ranges.

According to the fifth and sixth aspects of the invention, it is possible to carry out a temperature compensation of the constant voltage or a temperature variation compensation of the voltage difference between the inter-electrode voltages of the two control target cells based on the temperature detected by the temperature detecting unit.

According to the above aspects of the invention, it is possible to provide the gas sensor control device capable of improving precision in detecting the concentration of the specific gas component based on the output signal from the gas sensor element even when the characteristic of the voltage control unit mounted on the circuit board changes with a change in temperature of the circuit board.

BRIEF DESCRIPTION OF THE DRAWINGS

FIG. 6 shows an example of a map (table) stored on a ROM;

FIG. 7 shows another example of a map (table) stored on the ROM;

DETAILED DESCRIPTION OF THE PREFERRED EMBODIMENTS

Embodiments of the present invention is are next described with reference to the drawings. However, the present invention should not be construed as being limited thereto.

Figure 1:
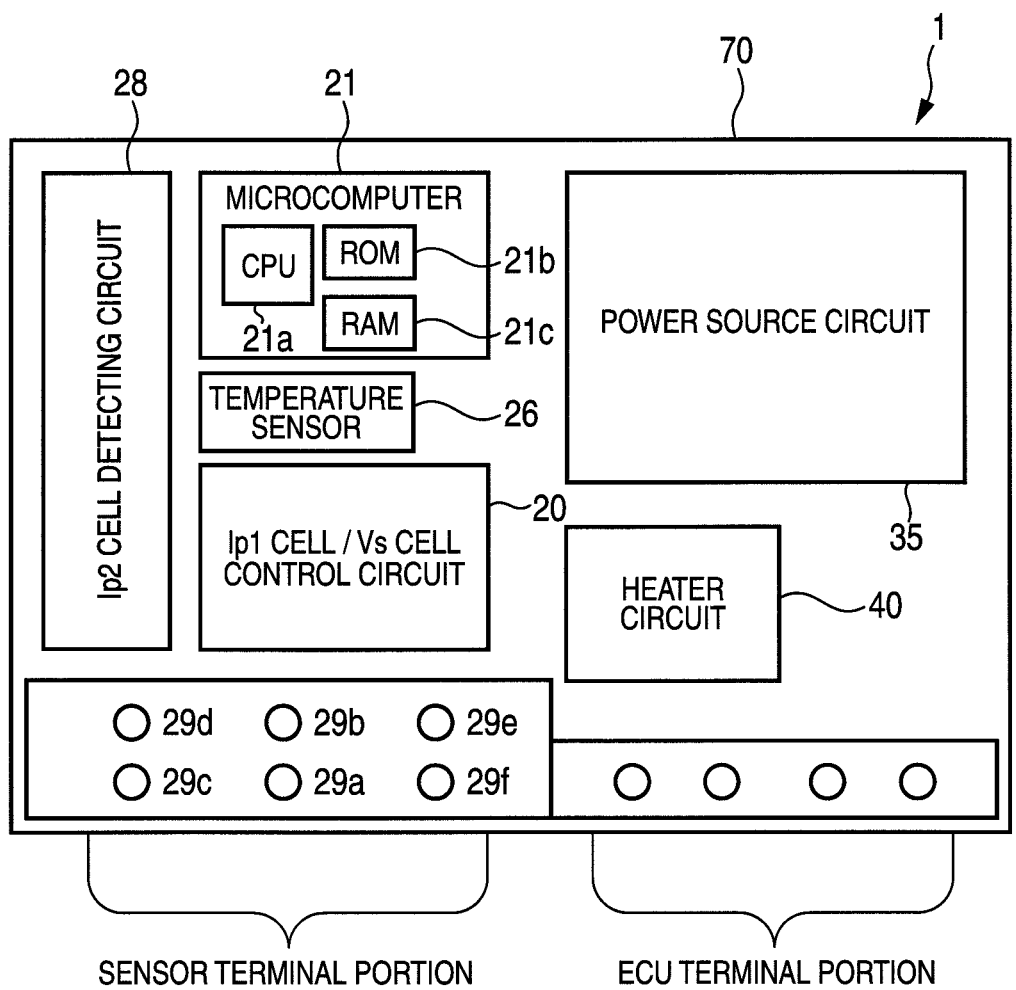
FIG. 1 is a block diagram of a $NO_x$ detecting device according to a first embodiment of the invention.

FIG. 1 is a block diagram of a gas sensor control device ($NO_x$ detecting device) 1 according to a first embodiment of the invention. The first embodiment of the invention shows an example of the above aspects of the invention in which first and second cells are provided, and a temperature-dependent variation in the voltage difference between the voltage developed across the electrodes of the first control target cell and the voltage developed across the electrodes of the second cell is compensated to keep the voltage difference constant. The first and second cells correspond to an oxygen concentration detecting cell and a second pumping cell, respectively.

The $NO_x$ detecting device 1 is mounted to a vehicle including an internal combustion engine (not shown, and hereinafter, referred to as an "engine"). The $NO_x$ detecting device 1 includes an Ip1 cell/Vs cell control circuit 20, a microcomputer (hereinafter, referred to as a "MC") 21, a temperature detecting unit (temperature sensor) 26, an Ip2 detecting circuit 28, a power source circuit 35, a heater circuit 40, sensor terminal portion 81 including terminals 29a to 29d, 42e, 42f, and an ECU terminal portion 82 including terminals, which are mounted on one circuit board 70. The sensor terminal portions are electrically connectable to the $NO_x$ sensor (specifically, an $NO_x$ sensor element 10), and the ECU terminal portion is electrically connectable to an engine control unit (hereinafter, referred to as a "ECU") provided on the vehicle. The $NO_x$ detecting device 1 is configured to convert a detection signal output from the $NO_x$ sensor ($NO_x$ sensor element 10) into a concentration signal using the $NO_x$ detecting device 1 (specifically, the MC 21) and transmits the concentration signal to the ECU. The ECU calculates the $NO_x$ concentration in exhaust gas based on the concentration signal for controlling an engine operation state or for purifying the $NO_x$ accumulated in a catalyst. The heater circuit 40 of the $NO_x$ detecting device 1 is connectable to a heater 50 in the $NO_x$ sensor element 10 (see FIG. 2) for controlling a temperature of the $NO_x$ sensor element 10.

The MC 21 controls the $NO_x$ detecting device 1 entirely and includes a CPU (central processing unit) 21a, a ROM (Read Only Memory) 21b, and a RAM (Random Access Memory) 21c. Programs stored on the ROM are executed by the CPU. The temperature sensor 26 includes a thermistor and is disposed on the circuit board 70 closer to the first control circuit 20 and the Ip2 detecting circuit 28 than the heater circuit 40.

As used herein, the expression "disposed closer to the circuit" indicates "disposed closer to a circuit group (including components mounted on the circuit) necessary to exhibit a purpose or a function of the circuit." In the case where a specific circuit (e.g., the circuit group on the circuit board) forms one region as a whole, the expression "the temperature detecting unit (the temperature sensor 26) disposed closer to the circuit" may include the temperature detecting unit (the temperature sensor 26) disposed within the region (for example, a space between the circuit wirings of the circuit group) in addition to a location outside of the boundary of the region. Here, the temperature detecting unit is preferably disposed within the region for compensating the control voltage based on the temperature detected by the temperature detecting unit.

Next, the $NO_x$ sensor connected to the $NO_x$ detecting device 1 includes the $NO_x$ sensor element 10, a housing accommodating the $NO_x$ sensor element 10, and a lead wire connected to the $NO_x$ sensor element 10. Hereinafter, the $NO_x$ sensor element 10 will be described with reference to FIG. 2 showing a cross-sectional view taken along a longitudinal direction of the $NO_x$ sensor element 10.

Figure 2:
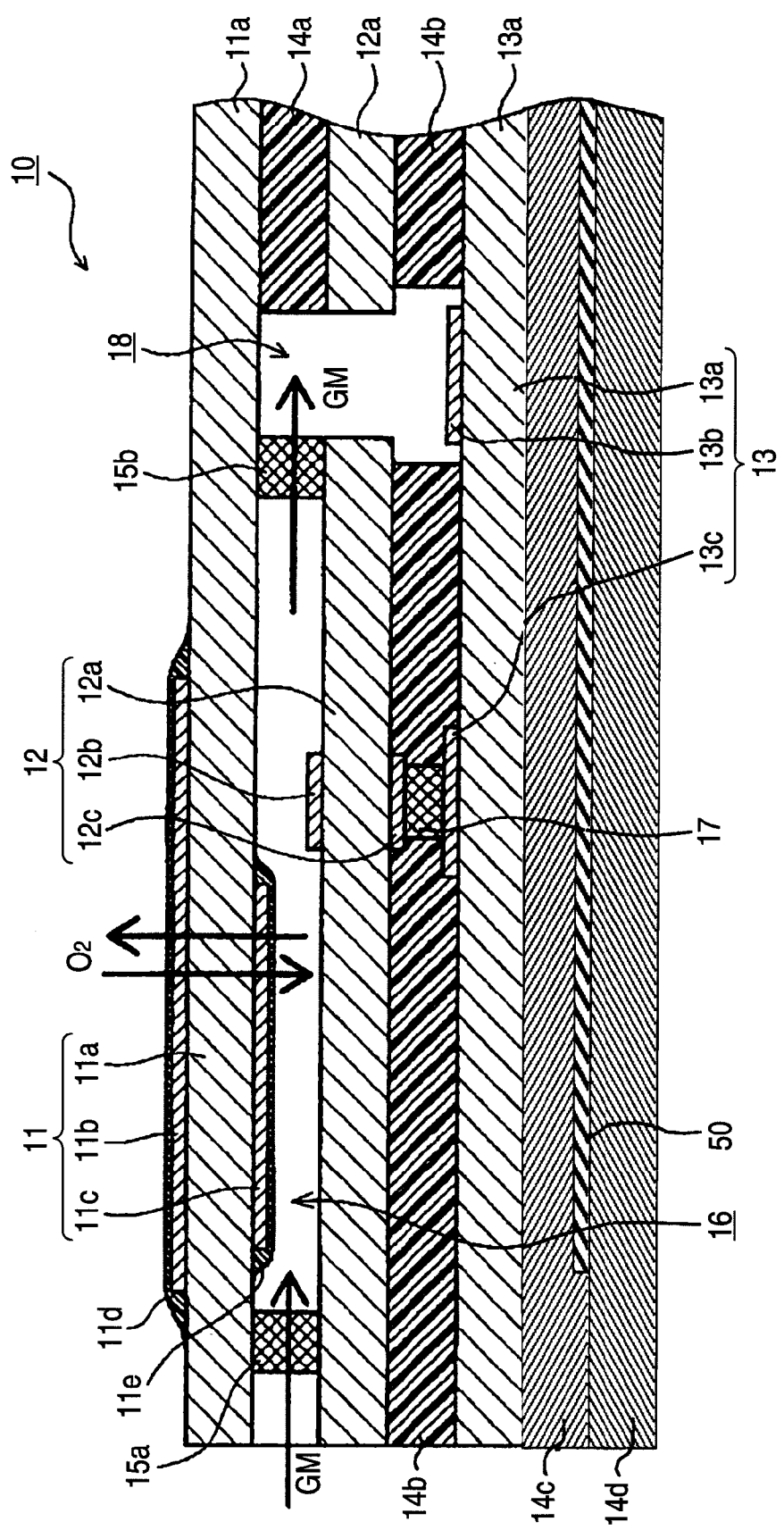
FIG. 2 is a cross-sectional view taken along a longitudinal direction of the $NO_x$ sensor element.

In FIG. 2, the $NO_x$ sensor element 10 includes a first solid electrolyte layer 11a, an insulation layer 14a, a second solid electrolyte layer 12a, an insulation layer 14b, a third solid electrolyte layer 13a and insulation layers 14c and 14d, which are sequentially laminated. A first measurement chamber 16 is defined between the first solid electrolyte layer 11a and the second solid electrolyte layer 12a. A gas to be measured GM is introduced into the first measurement chamber 16 from the outside via a first diffusion resistance 15a disposed on the left end (entrance) of the first measurement chamber 16.

A second diffusion resistance 15b is disposed on an end opposite to the entrance of the first measurement chamber 16. A second measurement chamber 18 communicating with the first measurement chamber 16 is defined on the right side of the first measurement chamber 16 with the second diffusion resistance 15b interposed therebetween. The second measurement chamber 18 penetrates the second solid electrolyte layer 12a and is defined between the first solid electrolyte layer 11a and the third solid electrolyte layer 13a.

The heater 50 having a long-plate shape is embedded between the insulation layers 14c and 14d and extends in the longitudinal direction of the $NO_x$ sensor element 10. The heater 50 raises a temperature of the gas sensor to an activation temperature for increasing the oxygen ion conductivity of the solid electrolyte layer and to thus stabilize its operation.

The insulation layers 14a to 14d mainly contain alumina, and the first diffusion resistance 15a and the second diffusion resistance 15b mainly contain a porous material such as alumina. The heater 50 contains platinum.

A first pumping cell 11 includes a first solid electrolyte layer 11a mainly containing zirconia having oxygen ion conductivity, a first inner pump electrode 11c and a first outer electrode 11b paired with the first inner pump electrode 11c. The first inner pump electrode 11c and the first outer electrode 11b sandwiches the first solid electrolyte layer 11a. The first inner pump electrode 11c is disposed in the first measurement chamber 16. The first inner pump electrode 11c and the first outer pump electrode 11b mainly contain platinum, and the outer surfaces thereof are respectively covered with protection layers 11e and 11d mainly containing a porous material.

Figure 3:
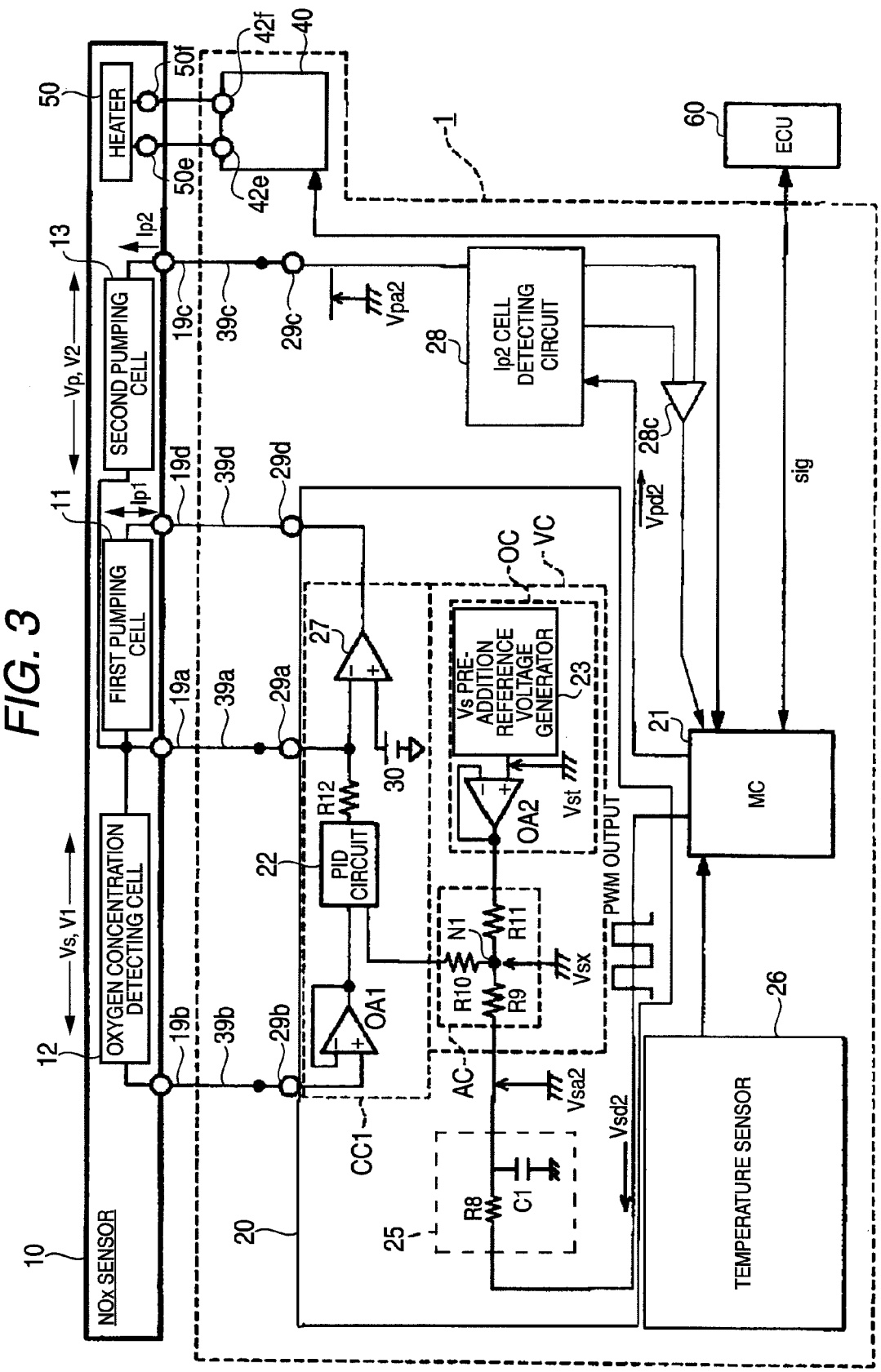
FIG. 3 is a circuit diagram showing of the $NO_x$ detecting device.

The first inner pump electrode 11c is connected to a first sensor terminal 19a, and the first outer pump electrode 11b is connected to a fourth sensor terminal 19d (see FIG. 3).

An oxygen concentration detecting cell 12 includes a second solid electrolyte layer 12a mainly containing zirconia, a detection electrode 12b, and a reference electrode 12c, the detection electrode 12b and the reference electrode 12c sandwiching the second solid electrolyte layer 12a. The detection electrode 12b is disposed in the first measurement chamber 16 on the downstream side of the first inner pump electrode 11c. The detection electrode 12b and the reference electrode 12c mainly contain platinum and are connected to the first sensor terminal 19a and the second sensor terminal 19b, respectively (see FIG. 3).

A portion of the insulation layer 14b is cut out such that the reference electrode 12c contacting the second solid electrolyte layer 12a is disposed in the cutout portion, and porous material is filled in the cutout portion thereby forming a reference oxygen chamber 17. Then, when a predetermined small amount of current flows from a constant current source not shown in FIG. 3 to the oxygen concentration detecting cell 12, oxygen moves from the first measurement chamber 16 to the reference oxygen chamber 17 for use as an oxygen reference.

A second pumping cell 13 includes a third solid electrolyte layer 13a mainly containing zirconia, a second inner pump electrode 13b disposed on a surface of the third solid electrolyte layer 13a facing the second measurement chamber 18, and a second pump counter electrode 13c as an electrode paired with the second inner pump electrode 13b. The second inner pump electrode 13b and the second pump counter electrode 13c mainly contain platinum and are respectively connected to a third sensor terminal 19c and the first sensor terminal 19a (see FIG. 3).

Additionally, the second pump counter electrode 13c is disposed on the third solid electrolyte layer 13a and in a cutout portion of the insulation layer 14b. The second pump counter electrode 13c is disposed in the reference oxygen chamber 17 and opposes the reference electrode 12c.

Next, an operation example of the $NO_x$ sensor element 10 will be described. First, when the engine is started and power is supplied from an external power source to the power source circuit 35, the heater 50 is operated via the heater circuit 40 so as to heat the first pumping cell 11, the oxygen concentration detecting cell 12 and the second pumping cell 13 up to an activation temperature. Subsequently, once the cells 11 to 13 reach the activation temperature, the first pumping cell 11 pumps out excess oxygen in the gas to be measured (exhausted gas) GM that has been introduced into the first measurement chamber 16 from the first inner pump electrode 11c toward the first counter electrode 11b.

The oxygen concentration in the first measurement chamber 16 corresponds to a voltage (inter-terminal voltage) Vs developed across electrodes 12b, 12c of the oxygen concentration detecting cell 12. Therefore, a first pump current Ip1 flowing to the first pumping cell 11 is controlled such that the inter-electrode voltage Vs assumes a constant voltage V1 (for example, 425 mV), to thereby adjust the oxygen concentration in the first measurement chamber 16 to a degree such that the $NO_x$ is not separated.

The gas to be measured GM having an adjusted oxygen concentration flows into the second measurement chamber 18. Subsequently, a constant voltage V2 (a value larger than a control voltage of the oxygen concentration detecting cell 12, for example, 450 mV) is applied across the electrodes of the second pumping cell 13 as inter-terminal voltage Vp. The applied constant voltage V2 separates the $NO_x$ gas in the gas to be measured GM into oxygen and $N_2$ gas. Accordingly, the $NO_x$ in the second measurement chamber 18 is separated into nitrogen and oxygen. Subsequently, a second pump current Ip2 flows through the second pumping cell 13 which is a measure of oxygen that has separated from $NO_x$ introduced into the second measurement chamber 18. Since the second pump current Ip2 is proportional to the concentration of $NO_x$, the concentration of $NO_x$ in the gas to be measured may be determined by detecting the second pump current Ip2.

Next, a circuit configuration of the $NO_x$ detecting device 1 will be described with reference to FIG. 3. The power source circuit 35 of FIG. 1 is not shown in FIG. 3.

The $NO_x$ detecting device 1 controls the current supply to the $NO_x$ sensor element 10 and transmits/receives various signals including the $NO_x$ concentration signal to/from the ECU 60. The $NO_x$ detecting device 1 is connected to the first pumping cell 11 of the $NO_x$ sensor element 10 via a first wiring 39a and a fourth wiring 39d. The $NO_x$ detecting device 1 is connected to the second pumping cell 13 via the first wiring 39a and the third wiring 39c. The $NO_x$ detecting device 1 is connected to the oxygen concentration detecting cell 12 via the first wiring 39a and a second wiring 39b.

The first wiring 39a to the fourth wiring 39d are connected to the first circuit terminal 29a to the fourth circuit terminal 29d of the $NO_x$ detecting device 1, respectively.

The heater circuit 40 is connected to the heater 50 via a fifth wiring 50e and a sixth wiring 50f.

In the $NO_x$ detecting device 1, the Ip1 cell/Vs cell control circuit 20 includes a PID (Proportional-Integral-Derivative) circuit 22, a Vs pre-addition reference voltage generator 23, a low-pass filter 25, an Ip1 driver 27, a plurality of resistors R9 to R12 and buffers (OP Amp) OA1 and OA2.

The buffer OA1 is configured to perform negative feedback, a non-invert input terminal (+) thereof is connected to a second circuit terminal 29b, and an output of the buffer OA1 is input to the PID circuit 22. Two input terminals of the PID circuit 22 are connected to an output terminal of the buffer OA1 and an output side of a reference voltage circuit VC, respectively. An output of the PID circuit 22 is input to an inverting input terminal (−) of the Ip1 driver 27 via the resistor R12. The output of the PID circuit 22 is also connected to the first circuit terminal 29a via the resistor R12.

The Ip1 driver 27 is an OP Amp configured to allow the first pump current Ip1 to flow to the first pumping cell 11 and including a non-invert input terminal (+) connected to a reference power source and an output terminal connected to the fourth circuit terminal 29d.

The first control circuit CC1 (corresponding to a voltage control unit connected to the oxygen concentration detecting cell 12) includes The buffer OA1, the PID circuit 22, a pre-addition reference voltage circuit OC, an addition circuit AC, a resistor R12, a reference power source 30, and the Ip1 driver 27. The first control circuit CC1 controls the inter-terminal voltage Vs of the oxygen concentration detecting cell 12 to a constant voltage V1.

The reference voltage circuit VC includes the pre-addition reference voltage circuit OC and the addition circuit AC.

The pre-addition reference voltage circuit OC includes the Vs pre-addition reference voltage generator 23 and the buffer OA2 including the non-inverting input terminal (+) connected to the output terminal of the Vs pre-addition reference voltage generator 23 configured to perform a negative feedback.

The addition circuit AC includes the resistors R9 to R11. A pre-addition reference voltage Vst output from the buffer OA2 and a correction voltage Vsa2 described below are added at a node N1, and a reference voltage Vsx produced therefrom is input to the PID circuit 22 via the resistor R10.

Next, operation of the first control circuit CC1 will be described. Based on the reference voltage Vsx at the node N1, the PID circuit 22 controls the inter-terminal voltage Vs between the first sensor terminal 19a and the second sensor terminal 19b of the oxygen concentration detecting cell 12 (a voltage between the detection electrode 12b and the reference electrode 12c) to a constant voltage V1 (in the present embodiment, 425 mV). Specifically, the output voltage of the PID circuit 22 is changed by performing a PID calculation using a deviation amount ΔVs of the inter-terminal voltage Vs.

The Ip1 driver 27 of the first control circuit CC1 controls the first pump current Ip1 flowing to the first pumping cell II. That is, since the output of the PID circuit 22 is input to the inverting input terminal (−) of the Ip1 driver 27, an input-output circuit of the Ip1 driver 27 forms a negative feedback circuit from the fourth circuit terminal 29d to the first circuit terminal 29a via the fourth wiring 39d, the first pumping cell II and the first wiring 39a. For this reason, the first pump current Ip1 flows to the first pumping cell 11 so that a potential V29a of the first circuit terminal 29a is equal to a reference potential of the reference power source 30 (in the present embodiment, 3.6 V).

As described above, the first control circuit CC1 forms a feedback control circuit including the oxygen concentration detecting cell 12 and the first pumping cell 11 via the first wiring 39a, the second wiring 39b and the fourth wiring 39d and performs a control operation to maintain the inter-terminal voltage Vs of the oxygen concentration detecting cell 12 at the constant voltage V1 (425 mV). Here, the value of the constant voltage V1 is the inter-terminal voltage Vs at a reference temperature (25° C.).

Meanwhile, the inter-terminal voltage Vp of the second pumping cell 13 is controlled to a constant voltage V2 by a second control circuit CC2 of the Ip2 detecting circuit 28. A control circuit, such as the first control circuit CC1 of the oxygen concentration detecting cell 12, is not used for the first pumping cell 11.

Figure 4:
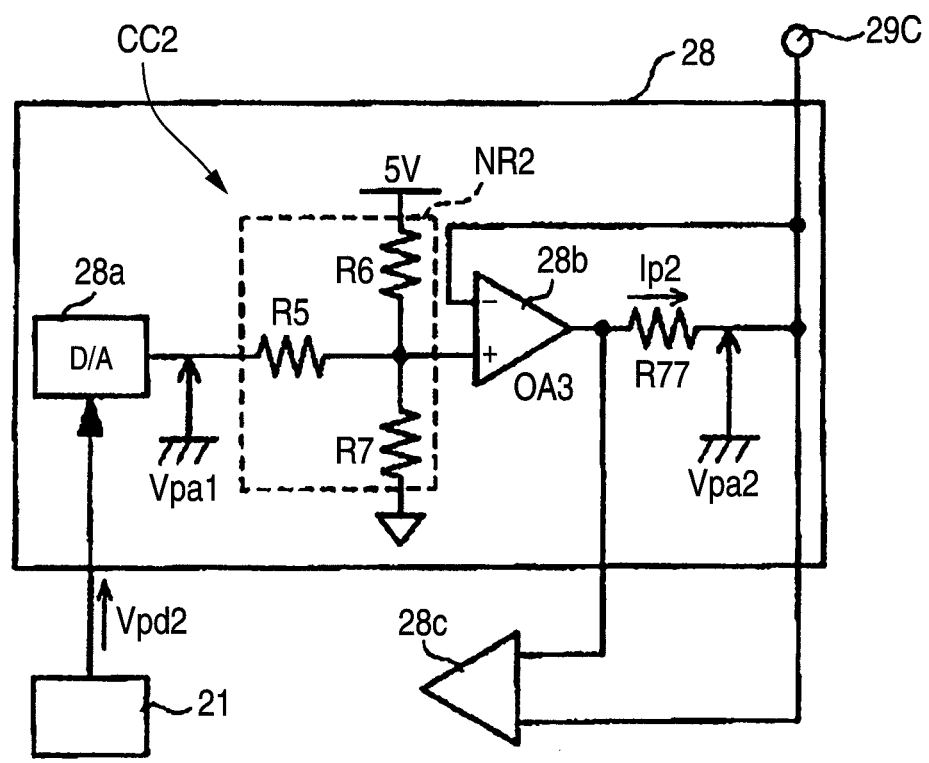
FIG. 4 is a circuit diagram showing an IP2 cell detecting circuit.

The second control circuit CC2 (corresponding to a voltage control unit connected to the second pumping cell 13) of the Ip2 detection circuit 28 has a configuration shown in FIG. 4. The second control circuit CC2 includes: a D/A converter 28a configured to convert a digital setting value Vpd2 output from the MC 21 into an analog setting voltage Vpa1. The second control circuit CC2 further includes: a potential control circuit NR2 including resistors R5 to R7 having substantially the same temperature characteristic and configured to control a potential of an analog set voltage Vpa1; and a predetermined voltage circuit 28b including a buffer OA3. An output of the buffer OA3 is input to an inverting input terminal (−) of the buffer OA3, and the analog set voltage Vpa1 is input to a non-inverting input terminal (+) via the potential control circuit NR2.

The Ip2 detection circuit 28 includes a resistor R77 connected to an output terminal of the buffer OA3 together with the second control circuit CC2. Both ends of the resistor R77 are connected to input terminals of a differential amplifier circuit 28c, respectively, and an output terminal of the differential amplifier circuit 28c is connected to the MC 21 (see FIG. 3). Accordingly, the second pump current Ip2 flowing to the second pumping cell 13 is converted into a voltage by the resistor R77, the voltage enters the MC 21 via the differential amplifier circuit 28c (see FIG. 3), and then the MC 21 calculates the concentration of $NO_x$ based on the output signal of the differential amplifier circuit (i.e., the second pump current Ip2).

The Ip2 detection circuit 28 (predetermined voltage circuit 28b) generates the analog voltage Vpa2 based on the analog set voltage Vpa1 obtained by the D/A converter 28a. The analog voltage Vpa2 is a set voltage calculated so that the inter-terminal voltage Vp of the second pumping cell 13 is equal to a constant voltage V2 (450 mV) and is directly applied to the second pumping cell 13 via the third sensor terminal 19c.

Here, a value of the constant voltage V2 is the inter-terminal voltage Vp at a reference temperature (25° C.).

In the case where the characteristics of electronic components mounted on the circuit board 70 of the $NO_x$ detecting device 1 and constituting the first control circuit CC1 and the second control circuit CC2 change due to a temperature variation of the circuit board 70, it is difficult to perform a control operation to maintain the inter-terminal voltage Vs of the oxygen concentration detecting cell 12 and the inter-terminal voltage Vp of the second pumping cell 13 at the constant voltages V1 and V2, respectively. Particularly, a leakage current or a voltage variation in the OP Amp easily occurs in accordance with a temperature variation.

Figure 5:
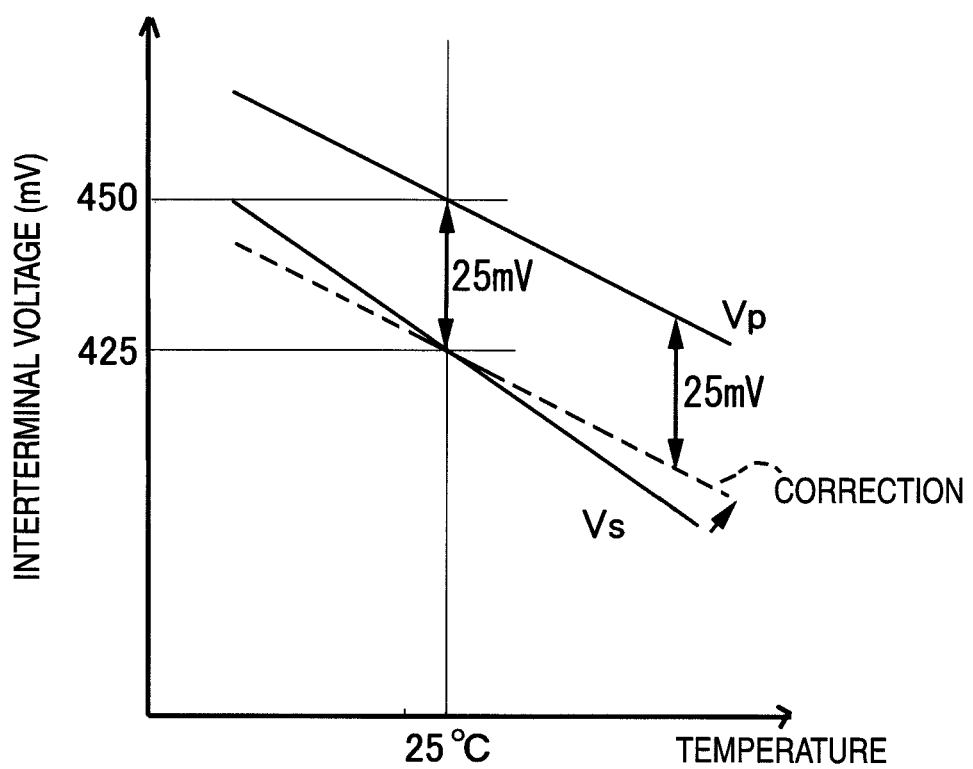
FIG. 5 is a graph illustrating variations in a voltage between terminals of an oxygen concentration detecting cell and in a voltage between terminals of a second pumping cell, in response to a change in a temperature in the vicinity of the $NO_x$ detecting device.

FIG. 5 shows a variation in inter-terminal voltages (Vs and Vp) of the oxygen concentration detecting cell 12 and the second pumping cell 13 in response to a temperature change in the vicinity of the $NO_x$ detecting device 1 (i.e., a temperature of the circuit board 70). It is understood that the voltage Vs or Vp changes depending on the temperature.

In this case, a temperature compensation may be carried out so that the inter-terminal voltages of the oxygen concentration detecting cell 12 and the second pumping cell 13 are maintained at the constant voltages V1 and V2, respectively, but the configuration of such a circuit is complicated. Accordingly, in the first embodiment, a temperature compensation is carried out so that the inter-terminal voltage difference (Vp−Vs) between the control target cells (the oxygen concentration detecting cell 12 and the second pumping cell 13) is maintained constant.

Particularly, in the $NO_x$ sensor element 10 according to the first embodiment, since the second pump current Ip2 flowing to the second pumping cell 13 depending on the concentration of the $NO_x$ is minute current (e.g., on the order of μAs), if the voltage (i.e., the inter-terminal voltage Vp) applied to the second pumping cell 13 is directly corrected, a not insignificant level of variation may result in response to correction of the second pump current Ip2 irrespective of the $NO_x$ concentration. For this reason, in the gas control device 1 connected to the $NO_x$ sensor element 10 according to the first embodiment, a correction (temperature compensation) is desirably carried out so that the inter-terminal voltage difference (Vp–Vs) is maintained constant without directly correcting the inter-terminal voltage Vp of the second pumping cell 13.

That is, as depicted by the dashed line shown in FIG. 5, the inter-terminal voltage Vs of the oxygen concentration detecting cell 12 is corrected such that the inter-terminal voltage difference (Vp–Vs) is maintained constant regardless of a temperature variation of the circuit board 70.

Therefore, in the first embodiment, the inter-terminal voltage Vs is corrected such that the reference voltage Vsx is changed based on the temperature detected by the temperature sensor 26, and the inter-terminal voltage difference (Vp –Vs) is maintained constant.

Specifically, the MC 21 obtains the measurement value of the temperature sensor 26, determines a Vs correction value based on a map storing a predetermined Vs correction value for each temperature level, and then outputs a pulse width modulation (PWM) signal Vsd2 in accordance with the determined Vs correction value. The PWM signal Vsd2 is converted into a correction voltage Vsa2 via the low-pass filter 25 including a resistor R8 and a condenser C1, and the correction voltage Vsa2 is input to the addition circuit AC. The correction voltage Vsa2 is added to the pre-addition reference voltage Vst input from the pre-addition reference voltage circuit OC to the addition circuit AC to thereby obtain the reference voltage Vsx, and the reference voltage Vsx is input to the PID circuit 22.

In the first embodiment, the voltage correction unit includes the CPU 21*a*, the low-pass filter 25 and the addition circuit AC.

FIGS. 6 and 7 show an example of a map (table) stored on the ROM 21*b* of the MC 21. FIG. 6 shows the reference map at a low temperature (35° C. or less). FIG. 7 shows the reference map at a high temperature (higher than 35° C.).

These maps store the Vs correction value for each temperature level. More specifically, the Vs correction value indicates an offset value for each temperature level with respect to the PWM signal Vsd2 at a reference temperature (25° C.). The Vs correction value for each temperature level is not an actual detection value, but a model value. That is, since the inter-terminal voltage Vs increases or decreases with an increase in temperature depending on the configuration of the circuit controlling the current supply to the $NO_x$ sensor detecting element 10 and mounted on the circuit board 70, several expected variation patterns of the inter-terminal voltage Vs are stored as the Vs correction model values on the map.

Specifically, the expected voltage variation patterns are classified into correction ranks 0 to 15, and the Vs correction value for each temperature level and each correction rank is stored on the map. The expected voltage variation patterns can be obtained by: measuring a voltage variation in a state where the concentration of $NO_x$ is 0 ppm and the concentration of oxygen is 0 ppm, the state being set by connecting the gas sensor control device 1 according to the first embodiment to external test equipment; and allowing 0 µA of current to flow from the external test equipment to the second pumping cell 13 and 0 µA of current to flow from the external test equipment to the first pumping cell 11.

For example, in case of the correction rank 0 shown in FIG. 6, a variation in inter-terminal voltage difference (Vp–Vs) with a reduction in temperature is compensated by increasing an offset value, that is, a duty ratio of the signal Vsd2, with reducing temperature. On the other hand, in case of the correction rank 15 shown in FIG. 6, a variation in inter-terminal voltage difference (Vp–Vs) is compensated by decreasing an offset value with reducing temperature.

Additionally, in each gas sensor control device, only one of the correction ranks is used. In this case, at the time of shipping the gas sensor control device, each gas sensor control device is connected to the external test equipment so that 0 µA of current flows from the external test equipment to the second pumping cell 13, and then 0 µA of current flows from the external test equipment to the first pumping cell 11. At this time, it is determined which one of voltage variation patterns of the correction ranks 0 to 15 is approximate to the obtained voltage variation pattern. Then, the determined correction rank is used for the gas sensor control device used in the test. For example, when a flag indicating the correction rank of the gas sensor control device is set on the map, the CPU of the MC 21 refers to data corresponding to one correction rank on the map.

For example, in the gas sensor control device using the correction rank 5, since the Vs correction value at the temperature of −30° C. detected by the temperature sensor 26 is +0.8 as shown in FIG. 6, the Vs correction value (0.8) is added to the duty ratio (in the present embodiment, 30%) at a reference temperature (25° C.), and the PWM signal Vsd2 capable of obtaining the duty ratio of 30.8% after the correction is output. Accordingly, the correction (temperature compensation) is performed so that the inter-terminal voltage difference (Vp–Vs) is maintained constant.

In the first embodiment, the Vs correction values are stored in the map for each of predetermined temperature ranges (e.g., consecutive 20° C. ranges). For example, in FIG. 6, the Vs correction values in a temperature range from 15 to 35° C. are the same. For this reason, in case where the MC 21 refers to the map based on the current detection value of the temperature sensor 26, if the temperature range is unchanged from the previous referenced detection value to the current detection value, the Vs correction value does not change. Therefore, it is unnecessary to update the duty ratio of the PWM signal Vsd2. That is, it is advantageous in that a load of the CPU 21*a* of the MC 21 is further reduced than a case in which the duty ratio of the PWM signal Vsd2 is calculated based on the detection value of the temperature sensor 26.

The Vs correction values according to the first embodiment are set so that the inter-terminal voltage difference (Vp–Vs) is maintained at a reference value (450–425=25 mV) at 25° C. Accordingly, even when the temperature of the circuit board 70 changes, it is possible to maintain the inter-terminal voltage difference between the second pumping cell 13 and the oxygen concentration detecting cell 12 to be approximately 25 mV all the time.

Figure 8:
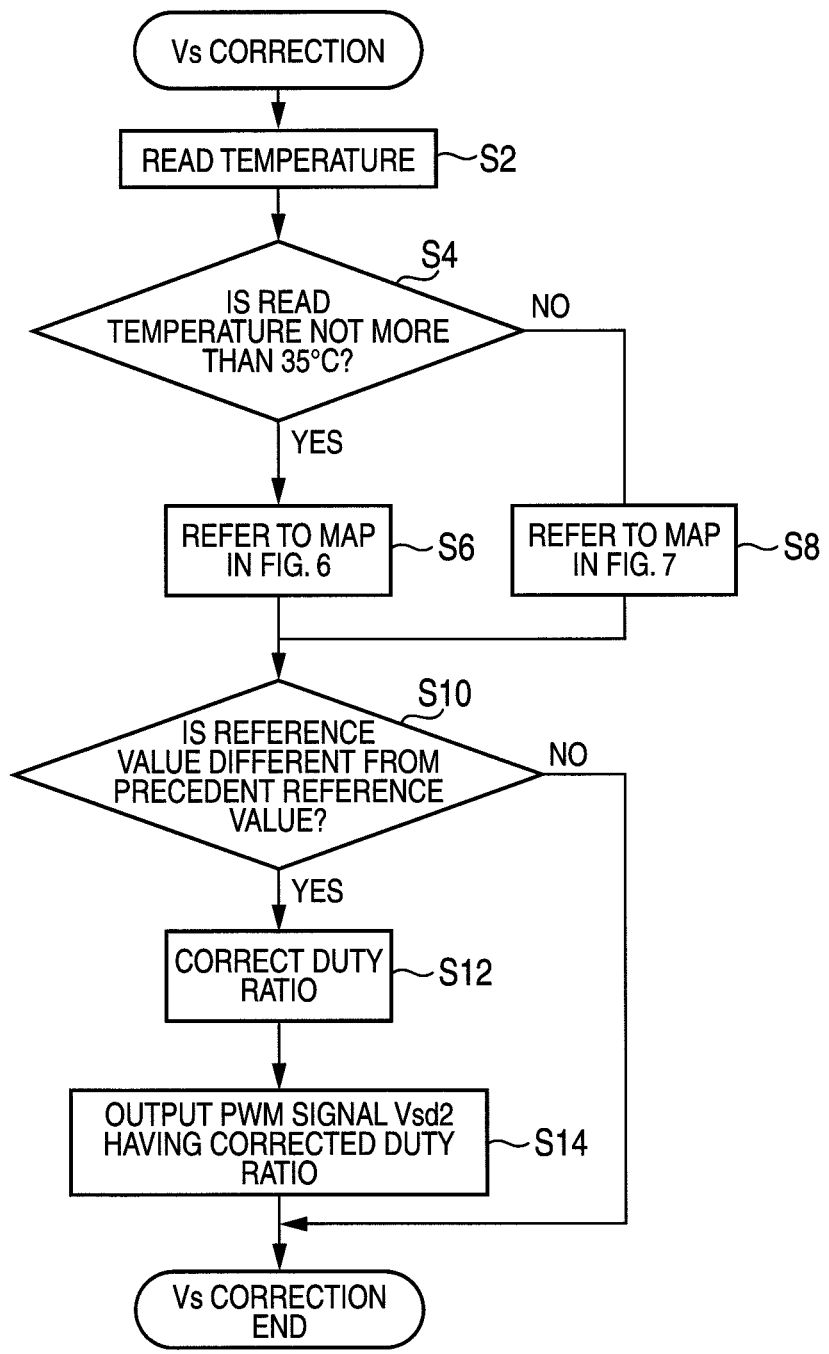
FIG. 8 is a flowchart explaining a correction process of an inter-terminal voltage Vs.

Next, with reference to FIG. 8, a correction process will be described in which the inter-terminal voltage difference (Vp–Vs) is maintained constant by the CPU 21*a* of the MC 21.

First, the CPU 21*a* reads the output of the temperature sensor 26 and calculates the detection temperature from the read value (Step S2). The A/D converter (not shown) of the MC 21 converts an analog output of the temperature sensor 26 into a digital value, and the digital value is read by the MC 21. Subsequently, the CPU 21*a* determines whether the calculated detection temperature is 35° C. or less (Step S4). If "Yes" at Step S4, the map shown in FIG. 6 is referred to based on the calculated detection temperature (Step S6). If "No" at Step S4, the map shown in FIG. 7 is referred to (Step S8).

Next, the CPU 21*a* determines whether the reference value (Vs correction value) at Step S6 or S8 is different from the previous referenced value (Step S10). For example, in a case where the temperature read by the CPU 21*a* at the previous timing is 18° C., the reference value shown in FIG. 6 is "0" (correction rank 5). In a case where the temperature read by the CPU 21a at the current timing is 27° C., the reference value in FIG. 6 is "0". Accordingly, in this case, it is "No" at Step S10.

If "Yes" at Step S10, the CPU 21a corrects the current duty ratio of the PWM signal Vsd2 based on the (current) referenced value (Step S12), and outputs the PWM signal Vsd2 having the corrected duty ratio (Step S14). Accordingly, the value of the reference voltage Vsx is adjusted such that the inter-terminal voltage difference (Vp−Vs) is maintained constant, and then the process ends.

On the other hand, if "No" at Step S10, the CPU 21a does not perform the correction, but the process ends.

Figure 9:
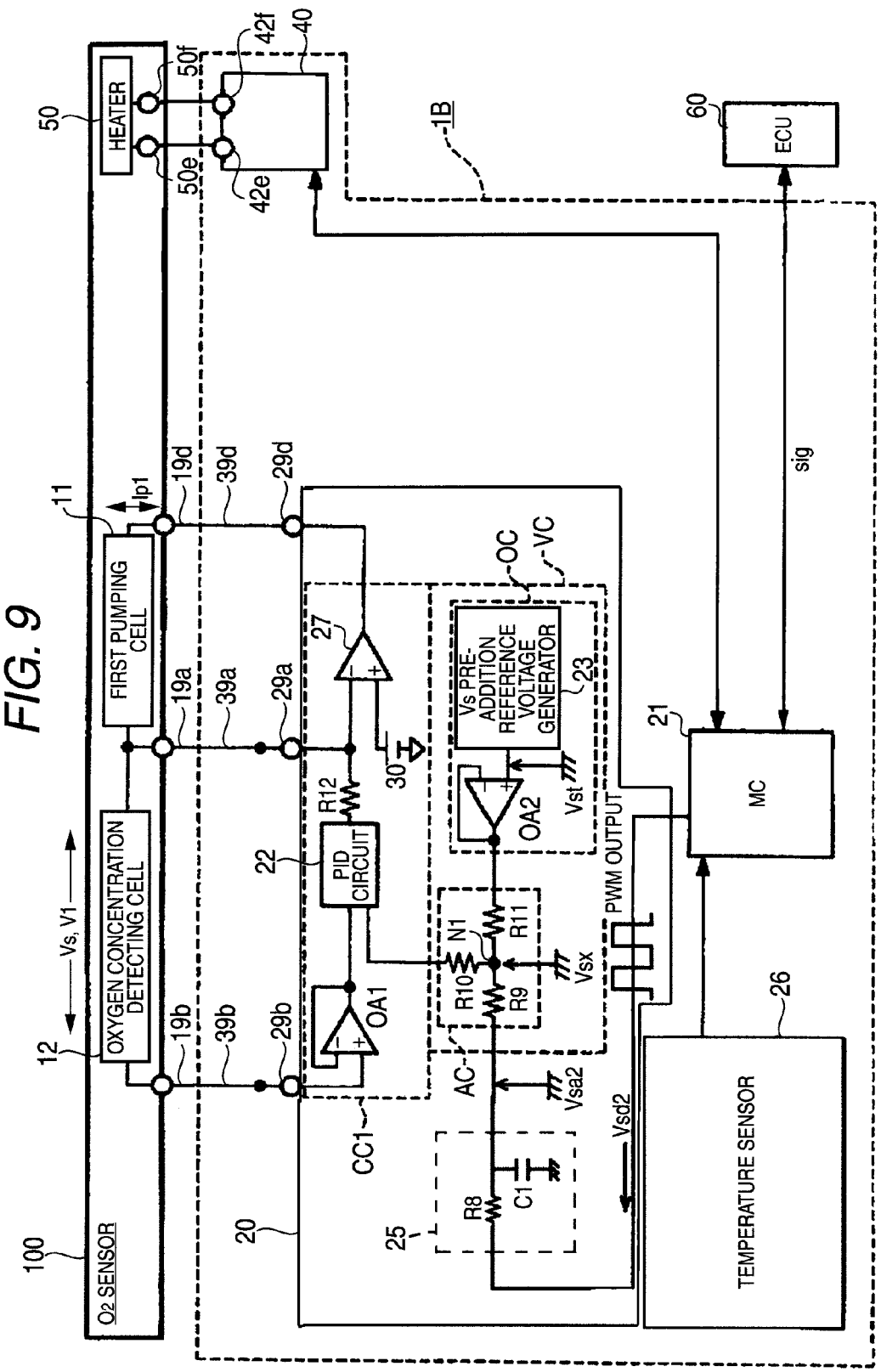
FIG. 9 is a circuit diagram showing an $O_2$ detecting device according to a second embodiment of the invention.

FIG. 9 is a block diagram illustrating a configuration of the gas sensor control device ($O_2$ detecting device) 1B according to a second embodiment of the invention. The second embodiment shows an example of temperature compensation for maintaining the inter-terminal voltage of one cell constant. In the second embodiment, the control target cell corresponds to the oxygen concentration detecting cell.

The gas sensor control device 1B is connected to a two-cell-type oxygen sensor element 100, and the oxygen sensor element 100 has the same configuration as that of the $NO_x$ sensor element 10 except that a second pumping cell 13 according to the first embodiment is not provided. Accordingly, this description will be omitted.

Further, the gas sensor control device 1B has the same configuration and operations as that of the gas sensor control device 1 according to the first embodiment, except that the Ip2 detecting circuit 28 for controlling the second pumping cell 13 is not provided. Accordingly, this description will be omitted.

Figure 10:
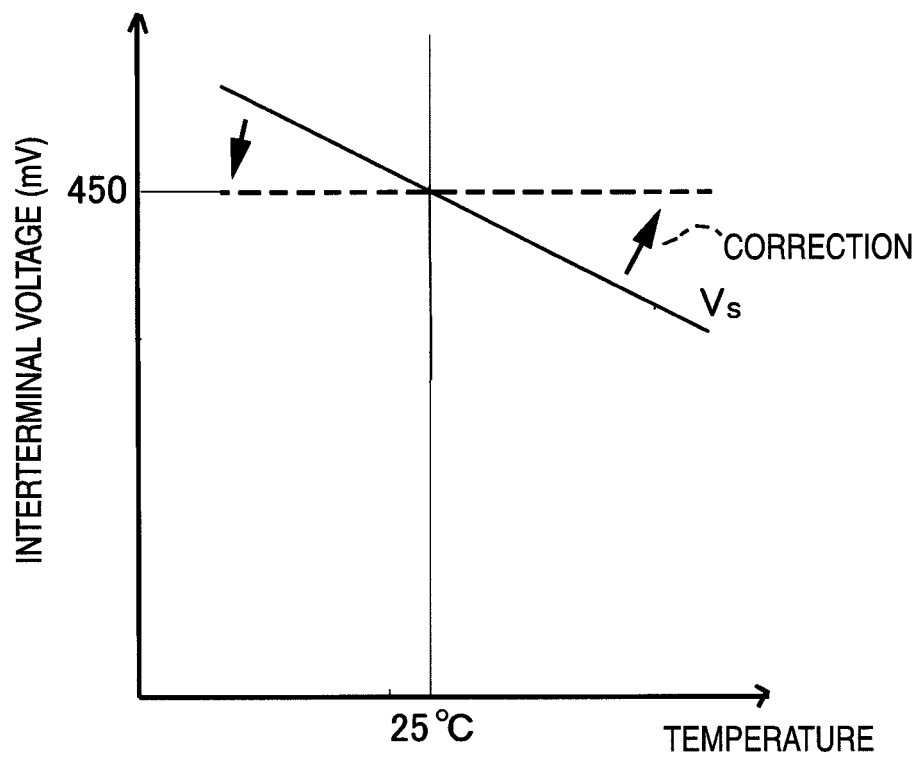
FIG. 10 is a graph illustrating a variation in a voltage between terminals of an oxygen concentration detecting cell in response to a change a temperature in the vicinity of the $O_2$ detecting device.

As shown in FIG. 10, the inter-terminal voltage Vs of the oxygen concentration detecting cell 12 changes with a change in temperature in the vicinity of the $O_2$ sensor detecting device (i.e., when the temperature of the circuit board 70) changes. In the second embodiment, the duty ratio of the PWM signal Vsd2 is controlled to correct the value of the reference voltage Vsx such that the inter-terminal voltage Vs of the oxygen concentration detecting cell 12 is maintained constant regardless of the temperature change at the circuit board. Accordingly, in the second embodiment, although the Vs correction value of the map (table) stored on the ROM 21b is different from that of the first embodiment, it is possible to use a method similar to the first embodiment for correcting the value of the reference voltage Vsx. This is done by referring to the Vs correction value from the map to update the duty ratio of the PWM signal Vsd2 in accordance with the detection value of the temperature sensor 26.

In the second embodiment, a temperature correction is carried out such that the inter-terminal voltage Vs is maintained equal to the inter-terminal voltage (425 mV) at a reference temperature (25° C.).

The present invention is not limited to the above-described embodiments, but various modifications and changes may be made within the scope and spirit of the claims appended hereto. For example, in the above embodiments, the Vs correction values is stored in the map for each of the predetermined temperature ranges, but the Vs correction values may be stored in the map for each degree of temperature. Further, in the above-described embodiments, the $NO_x$ sensor element includes three solid electrolyte layers but may include only two layers. An $NO_x$ sensor element including two solid electrolyte layers is disclosed, for example, in U.S. Pat. No. 5,942,190 (FIG. 2 and accompanying description) incorporated herein by reference.

The present invention is applicable to a gas sensor for detecting the concentration of $NO_x$ gas in the combustion gas of a boiler or exhaust gas of various internal-combustion engines or vehicles, and is also applicable to an oxygen sensor such as a wide-range air-fuel ratio sensor, but the invention is not limited thereto. For example, the present invention may be applied to a gas sensor including a gas sensor element for measuring the concentration of gas component(s) other than the $NO_x$, such as $CO_x$, $H_2O$, $H_2$, etc.

This application is based on Japanese patent Application No. 2007-287238 filed Nov. 5, 2007, the above application incorporated herein by reference in its entirety.

What is claimed is:

1. A gas sensor control device for controlling a gas sensor, said gas sensor comprising a gas sensor element including a cell comprising a solid electrolyte and a pair of electrodes disposed on the solid electrolyte for detecting concentration of a specific gas component, said gas sensor control device comprising:
   a circuit board electrically connectable to the gas sensor via an electrical conductor;
   a voltage control unit mounted on the circuit board and configured to control a voltage developed across the pair of electrodes of the cell to a constant voltage;
   a temperature detecting unit mounted on the circuit board and configured to detect a temperature of the circuit board; and
   a voltage correcting unit mounted on the circuit board and configured to apply a correction voltage to the voltage control unit compensating for a temperature-dependent variation in the level of the constant voltage based on the temperature detected by the temperature detecting unit,
   wherein the gas sensor element comprises a plurality of the cells including a first cell and a second cell,
   wherein said gas sensor further comprises a plurality of the voltage control units comprising a first voltage control unit and a second voltage control unit connected to the first cell and the second cell, respectively, the first voltage control unit and the second voltage control unit configured to maintain the voltage developed across the pair of electrodes of the first cell and developed across the second cell to first and second constant voltages, respectively, and
   wherein the voltage correcting unit is configured to apply the correction voltage to only one of the first voltage control unit and the second voltage control unit based on the temperature detected by the temperature detecting unit, the correction voltage compensating a temperature-dependent variation in a voltage difference between the voltage developed across the pair of electrodes of the first cell and the voltage developed across the pair of electrodes of the second cell, and
   an inter-terminal voltage difference is maintained constant regardless of a temperature variation of the circuit board.

2. The gas sensor control device according to claim 1, wherein the gas sensor element is an $NO_x$ sensor element comprising:
   first, second and third solid electrolyte layers in sequential order spaced apart from one another, said first solid electrolyte being exposed to an atmosphere outside of the gas sensor element and said second and third solid electrolyte layers being laminated in the gas sensor element;

a first measurement chamber defined between the first solid electrolyte and the second solid electrolyte;

a second measurement chamber in communication with the first measurement chamber;

an oxygen concentration detecting cell comprising: a detection electrode contacting the second solid electrolyte and exposed to the first measurement chamber; and a reference electrode paired with the detection electrode and exposed to a reference atmosphere, the oxygen concentration detecting cell being configured to generate an electromotive force in response to the concentration of oxygen in the first measurement chamber;

a first pumping cell comprising: a first inner pump electrode contacting the first solid electrolyte and exposed to the first measurement chamber; and an electrode paired with the first inner pump electrode, the first pumping cell configured to pump oxygen into or out of a gas to be measured introduced into the first measurement chamber such that the electromotive force generated in the oxygen concentration detecting cell is maintained at a first constant voltage; and a second pumping cell comprising: a second inner pump electrode contacting the third solid electrolyte and exposed to the second measurement chamber; and a second outer pump electrode paired with the second inner pump electrode and disposed outside the second measurement chamber, wherein a current flows through the second pumping cell in response to $NO_x$ concentration in the second measurement chamber when a second constant voltage is applied across the second inner pump electrode and the second outer pump electrode, wherein the first cell and the second cell correspond to the oxygen concentration detecting cell and the second pumping cell, respectively, and wherein the voltage correcting unit applies the correction voltage to the first voltage control unit connected to the oxygen concentration detecting cell.

3. The gas sensor control device according to claim 1, wherein the gas sensor element is an $NO_x$ sensor element comprising:

a first solid electrolyte exposed to an atmosphere outside of the gas sensor element;

a second solid electrolyte layer laminated in the gas sensor element and spaced apart from the first solid electrolyte;

a first measurement chamber defined between the first solid electrolyte and the second solid electrolyte;

a second measurement chamber in communication with the first measurement chamber;

an oxygen concentration detecting cell comprising: a detection electrode contacting the first solid electrolyte and exposed to the first measurement chamber; and a reference electrode paired with the detection electrode and exposed to a reference atmosphere, the oxygen concentration detecting cell being configured to generate an electromotive force in response to the concentration of oxygen in the first measurement chamber;

a first pumping cell comprising: a first inner pump electrode contacting the first solid electrolyte and exposed to the first measurement chamber; and an electrode paired with the first inner pump electrode, the first pumping cell configured to pump oxygen into or out of a gas to be measured introduced into the first measurement chamber such that the electromotive force generated in the oxygen concentration detecting cell is maintained at a first constant voltage; and a second pumping cell comprising: a second inner pump electrode contacting the second solid electrolyte and exposed to the second measurement chamber; and a second outer pump electrode paired with the second inner pump electrode and disposed outside the second measurement chamber, wherein a current flows through the second pumping cell in response to $NO_x$ concentration in the second measurement chamber when a second constant voltage is applied across the second inner pump electrode and the second outer pump electrode, wherein the first cell and the second cell correspond to the oxygen concentration detecting cell and the second pumping cell, respectively, and wherein the voltage correcting unit applies the correction voltage to the first voltage control unit connected to the oxygen concentration detecting cell.

4. The gas sensor control device according to claim 1, wherein the gas sensor comprises a heater configured to heat the gas sensor element, wherein the gas sensor control device further comprises a heater control unit configured to control a current supplied to the heater, and wherein the temperature detecting unit is disposed on the circuit board closer to the voltage control unit than the heater control unit.

5. The gas sensor control device according to claim 1, further comprising:

a storage unit in which correction values corresponding to the correction voltage are stored in association with the temperature.

6. The gas sensor control device according to claim 5, wherein correction values are stored in the storage unit for each of predetermined temperature ranges.

* * * * *